(12) United States Patent
Crockett

(10) Patent No.: US 8,764,784 B2
(45) Date of Patent: *Jul. 1, 2014

(54) TATTOO NEEDLE HOUSING AND ASSEMBLY

(71) Applicant: Derek S. Crockett, Charlotte, NC (US)

(72) Inventor: Derek S. Crockett, Charlotte, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 13/861,736

(22) Filed: Apr. 12, 2013

(65) Prior Publication Data

US 2013/0238008 A1    Sep. 12, 2013

Related U.S. Application Data

(63) Continuation-in-part of application No. 12/967,464, filed on Dec. 14, 2010, now Pat. No. 8,449,567, and a continuation-in-part of application No. 12/778,558, filed on May 12, 2010, now Pat. No. 8,454,643.

(60) Provisional application No. 61/177,910, filed on May 13, 2009.

(51) Int. Cl.
*A61B 17/34* (2006.01)

(52) U.S. Cl.
USPC ................................ 606/186; 81/9.22

(58) Field of Classification Search
USPC .............. 606/131, 116, 186, 211; 81/9.22
See application file for complete search history.

(56) References Cited

U.S. PATENT DOCUMENTS

| 6,588,301 | B1 | 7/2003 | Chanet et al. |
| 8,449,567 | B2* | 5/2013 | Crockett ................ 606/186 |
| 8,454,643 | B2* | 6/2013 | Crockett ................ 606/186 |
| 2004/0186501 | A1 | 9/2004 | Su |
| 2007/0038181 | A1* | 2/2007 | Melamud et al. ........ 604/158 |

* cited by examiner

*Primary Examiner* — Victor Nguyen
(74) *Attorney, Agent, or Firm* — Clements Bernard PLLC; Christopher L. Bernard; Lawrence A. Baratta, Jr.

(57) ABSTRACT

The present invention provides a tattoo needle housing, including: a substantially hollow structure configured to surround a plurality of tattoo needles, wherein the substantially hollow structure includes a bottom edge portion at one end thereof that has a shape that substantially matches and conforms to a collective shape of the tips of the plurality of tattoo needles taken as a group, wherein the substantially hollow structure includes one or more ports manufactured into one or more of a top surface and a bottom surface thereof, and wherein the substantially hollow structure includes an end wall adjacent to the tips of the plurality of tattoo needles configured to form a reservoir to retain ink adjacent to the plurality of tattoo needles.

6 Claims, 9 Drawing Sheets

TATTOO NEEDLE HOUSING AND ASSEMBLY

CROSS-REFERENCE TO RELATED APPLICATION(S)

The present patent application/patent is a continuation-in-part of co-pending U.S. patent application Ser. No. 12/967,464, filed on Dec. 14, 2010, and entitled "TATTOO NEEDLE HOUSING AND ASSEMBLY," which is a continuation-in-part of co-pending U.S. patent application Ser. No. 12/778,558, filed on May 12, 2010, and entitled "TATTOO NEEDLE HOUSING AND ASSEMBLY," which claims the benefit of priority of U.S. Provisional Patent Application No. 61/177,910, filed on May 13, 2009, and entitled "CURVED TIP TATTOO NEEDLE HOUSING," the contents of all of which are incorporated in full by reference herein.

FIELD OF THE INVENTION

The present invention relates generally to the field of tattoo equipment. More specifically, the present invention relates to a tattoo needle housing and assembly. The tattoo needle housing includes a novel reservoir feature for holding and retaining ink during the tattooing process and the tattoo needle housing assembly includes a novel tip having a curvature that substantially matches the collective curvature of a plurality of enclosed tattoo needles.

BACKGROUND OF THE INVENTION

Tattoos are created by injecting ink into the skin. A tattoo artist employs a tattoo machine for creating a tattoo. Typically, the tattoo machine includes alternating electromagnetic coils that are used to move or vibrate one or more reciprocating tattoo needles that inject the ink into the skin. Each of the tattoo needles punctures the skin between 50 and 3,000 times per minute, and penetrates the skin by approximately a millimeter. Each of the tattoo needles injects the ink into the corresponding penetration holes, creating a permanent marking of the skin.

FIGS. 1-3 illustrate a plurality of tattoo needles in a curved tip arrangement (FIG. 1), a magnum ("mag") tube for holding and surrounding the plurality of tattoo needles (FIG. 2), and a plurality of different sized mag tubes (FIG. 3), respectively. The plurality of tattoo needles in the curved tip arrangement, as illustrated FIG. 1, include outside tattoo needles that are recessed axially relative to inside tattoo needles. This curved tip arrangement prevents tissue damage that occurs with a substantially flat profile on the tattoo needle tip (corresponding to the substantially flat housing profiles of FIGS. 2 and 3). Disadvantageously, ink distribution is uneven and there is still anatomical damage from the outside tattoo needles when a curved tip tattoo needle arrangement is utilized with a substantially flat housing profile mag tip or tube, as illustrated in FIGS. 2 and 3. In such an assembly, the outside tattoo needles are typically flush with the opening of the housing, while the inside tattoo needles typically protrude from the housing to a predetermined degree. Thus, what is still needed in the art is a tattoo needle housing assembly that includes a novel tip having a curvature that substantially matches the collective curvature of the plurality of enclosed tattoo needles.

FIG. 4 illustrates a conventional exemplary tattoo needle housing which consists of a prismatic tubular structure in which one or more rows, or a grouping of tattoo needles in a predetermined configuration, whether flat tipped or curved tipped, are disposed. In operation, the tattoo needle housing is dipped in ink and the ink wicks up the prismatic tubular structure and surrounds the tattoo needles. The ink is subsequently deposited by gravity and/or vibration. Disadvantageously, such tattoo needle housing tends to shed ink and run dry too quickly. Thus, what is still needed in the art is a tattoo needle housing that is configured to better retain ink.

BRIEF SUMMARY OF THE INVENTION

In various exemplary embodiments, the present invention provides a tattoo needle housing assembly that includes a novel tip having a curvature or shape that substantially matches the collective curvature or shape of a plurality of enclosed tattoo needles. In various exemplary embodiments, the present invention also provides a tattoo needle housing that includes a discrete cut away portion, or window or port, that, in part, forms a reservoir for more effectively retaining ink adjacent to the tattoo needles disposed in the tattoo needle housing.

In one exemplary embodiment, the present invention provides a tattoo needle housing, including: a substantially hollow prismatic structure configured to surround a plurality of tattoo needles, wherein the substantially hollow prismatic structure includes a bottom edge portion at one end thereof that has a curvature that substantially matches a collective curvature of the tips of the plurality of tattoo needles. Optionally, the substantially hollow prismatic structure further includes at least one side edge portion at one end thereof that has a curvature that substantially matches a collective curvature of the tips of the plurality of tattoo needles. Optionally, the substantially hollow prismatic structure further includes a top edge portion at one end thereof that has a curvature that substantially matches a collective curvature of the tips of the plurality of tattoo needles. Optionally, the substantially hollow prismatic structure is manufactured from titanium.

In another exemplary embodiment, the present invention provides a tattoo needle housing assembly, including: a plurality of tattoo needles; and a substantially hollow prismatic structure configured to surround the plurality of tattoo needles, wherein the substantially hollow prismatic structure includes a bottom edge portion at one end thereof that has a curvature that substantially matches a collective curvature of the tips of the plurality of tattoo needles. Optionally, the substantially hollow prismatic structure further includes at least one side edge portion at one end thereof that has a curvature that substantially matches a collective curvature of the tips of the plurality of tattoo needles. Optionally, the substantially hollow prismatic structure further includes a top edge portion at one end thereof that has a curvature that substantially matches a collective curvature of the tips of the plurality of tattoo needles. Optionally, the substantially hollow prismatic structure is manufactured from titanium.

In a further exemplary embodiment, the present invention provides a tattoo needle housing, including: a substantially hollow prismatic structure configured to surround a plurality of tattoo needles, wherein the substantially hollow prismatic structure includes a bottom edge portion at one end thereof that has a shape that substantially matches a collective shape of the tips of the plurality of tattoo needles, and wherein the substantially hollow prismatic structure includes an opening manufactured into one or more of a top surface and a bottom surface thereof. Optionally, the substantially hollow prismatic structure further includes at least one side edge portion at one end thereof that has a curvature that substantially matches a collective curvature of the tips of the plurality of tattoo needles. Optionally, the substantially hollow prismatic structure further includes a top edge portion at one end thereof that has a curvature that substantially matches a collective curvature of the tips of the plurality of tattoo needles. Optionally, the substantially hollow prismatic structure is manufactured from titanium.

In a still further exemplary embodiment, the present invention provides a tattoo needle housing, including: a substantially hollow structure configured to surround a plurality of tattoo needles, wherein the substantially hollow structure includes a bottom edge portion at one end thereof that has a shape that substantially matches a collective shape of the tips of the plurality of tattoo needles, and wherein the substantially hollow structure includes an opening manufactured into one or more of a top surface and a bottom surface thereof. Optionally, the substantially hollow structure also includes at least one side edge portion at one end thereof that has a curvature that substantially matches a collective curvature of the tips of the plurality of tattoo needles. Optionally, the substantially hollow structure further includes a top edge portion at one end thereof that has a curvature that substantially matches a collective curvature of the tips of the plurality of tattoo needles. Optionally, the substantially hollow structure includes a plurality of openings manufactured into one or more of the top surface and the bottom surface thereof Preferably, the substantially hollow structure includes and end wall that, along with the bottom edge portion, forms a port by which access to the plurality of tattoo needles is had from the exterior of the substantially hollow structure.

In a still further exemplary embodiment, the present invention provides a tattoo needle housing, including: a substantially hollow structure configured to surround a plurality of tattoo needles, wherein the substantially hollow structure includes a bottom edge portion at one end thereof that has a shape that substantially matches and conforms to a collective shape of the tips of the plurality of tattoo needles taken as a group, wherein the substantially hollow structure includes one or more ports manufactured into one or more of a top surface and a bottom surface thereof, and wherein the substantially hollow structure includes an end wall adjacent to the tips of the plurality of tattoo needles configured to form a reservoir to retain ink adjacent to the plurality of tattoo needles. Optionally, the substantially hollow structure also includes at least one side edge portion at one end thereof that has a shape that substantially matches a collective shape of the tips of the plurality of tattoo needles. Optionally, the substantially hollow structure further includes a top edge portion at one end thereof that has a shape that substantially matches a collective shape of the tips of the plurality of tattoo needles. Optionally, the substantially hollow structure is manufactured from a non-metallic material. Optionally, the substantially hollow structure includes a plurality of ports manufactured into one or more of the top surface and the bottom surface thereof The substantially hollow structure includes the end wall that, along with the bottom edge portion, forms a port by which access to the plurality of tattoo needles is had from the exterior of the substantially hollow structure.

BRIEF DESCRIPTION OF THE DRAWINGS

The present invention is illustrated and described herein with reference to the various drawings, in which like reference numbers denote like assembly components, and in which.

DETAILED DESCRIPTION OF THE INVENTION

Again, in various exemplary embodiments, the present invention provides a tattoo needle housing assembly that includes a novel tip having a curvature or shape that substantially matches the collective curvature or shape of a plurality of enclosed tattoo needles. In various exemplary embodiments, the present invention also provides a tattoo needle housing that includes a discrete cut away portion, or window or port, that, in part, forms a reservoir for more effectively retaining ink adjacent to the tattoo needles disposed in the tattoo needle housing.

Figure 1:
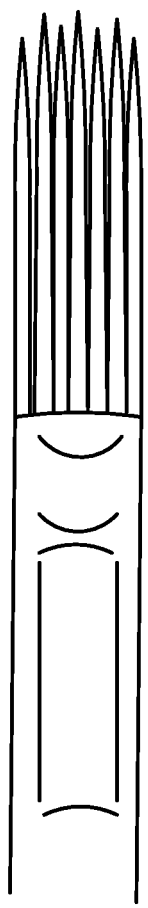
FIG. 1 illustrates a plurality of tattoo needles for use in a tattoo machine, the plurality of tattoo needles arranged in a curved tip configuration.
Figure 2:
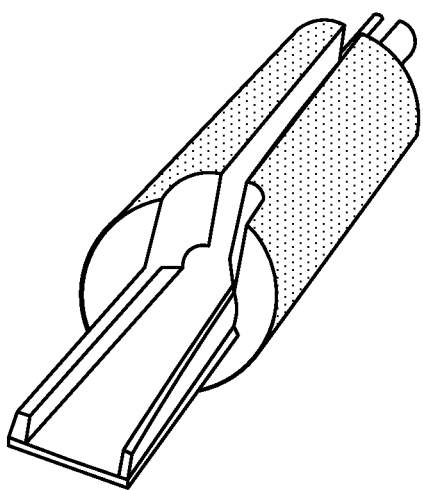
FIG. 2 illustrates one exemplary type of tattoo needle housing for use in a tattoo machine, the tattoo needle housing having a fully open top portion.
Figure 3:
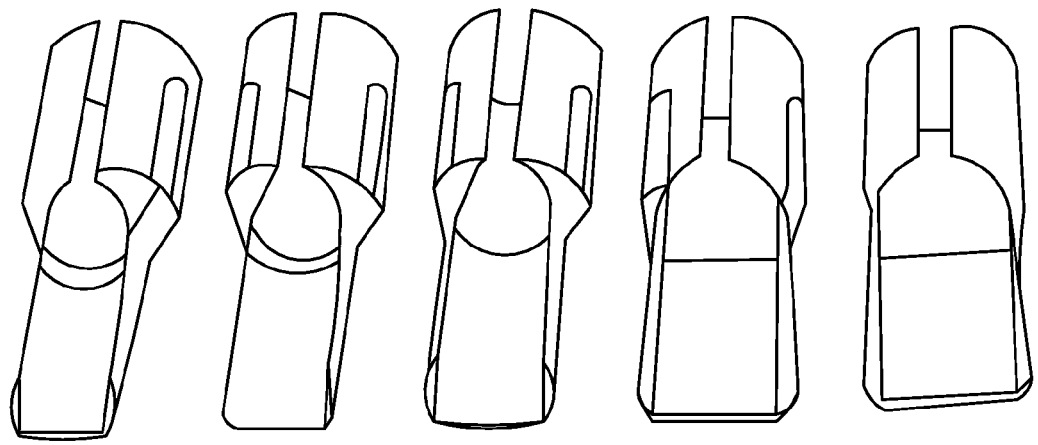
FIG. 3 illustrates additional exemplary types of tattoo needle housings for use in a tattoo machine, the tattoo needle housings each also having a fully open top portion.
Figure 4:
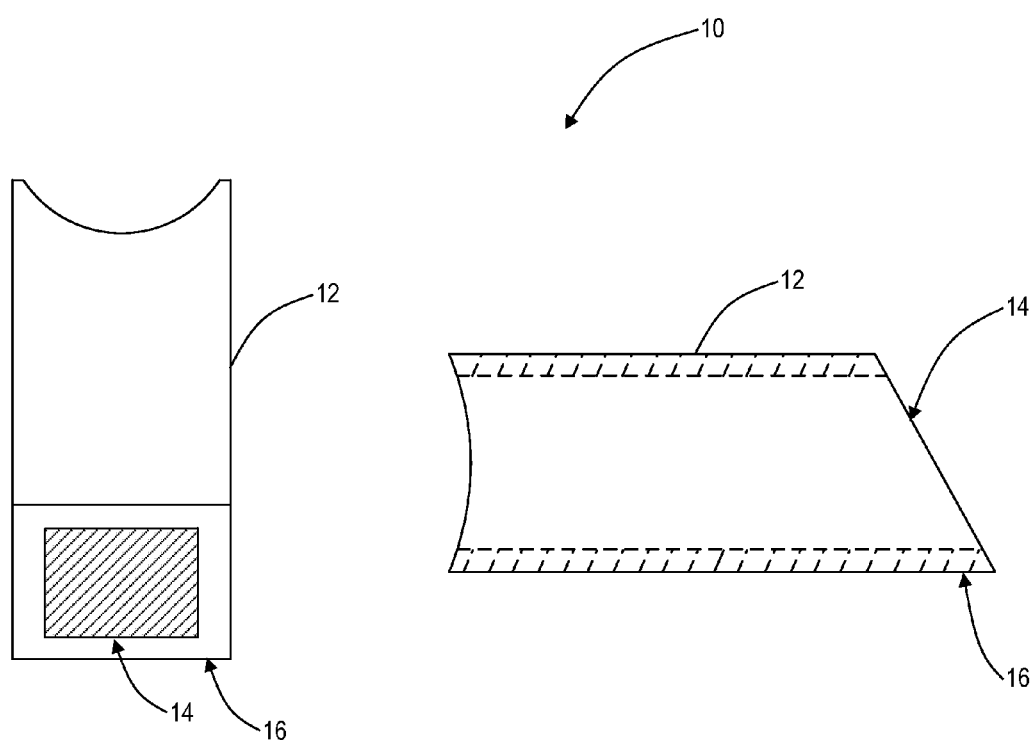
FIG. 4 illustrates a further exemplary type of tattoo needle housing for use in a tattoo machine, the tattoo needle housing having a fully closed top portion.

Referring to FIG. 4, a conventional tattoo needle housing 10 includes a prismatic tubular structure 12 that surrounds a plurality of tattoo needles (not illustrated) disposed therein. The prismatic tubular structure 12 may have a substantially rectangular shape, a substantially square shape, a substantially oval shape, a substantially circular shape, a substantially triangular shape, an odd shape, etc. The tip of each of the plurality of tattoo needles protrudes slightly through an opening 14 manufactured into the end portion of the prismatic tubular structure 12, such that the tip of each of the plurality of tattoo needles may selectively contact the skin of a tattoo recipient. The bottom-front edge 16 of the prismatic tubular structure 12 typically has a substantially square edge, substantially perpendicular to the axis of the prismatic tubular structure 12. In some cases, the shape of this bottom-front edge 16 substantially corresponds to the collective squared off tip configuration of the plurality of tattoo needles.

Figure 5:
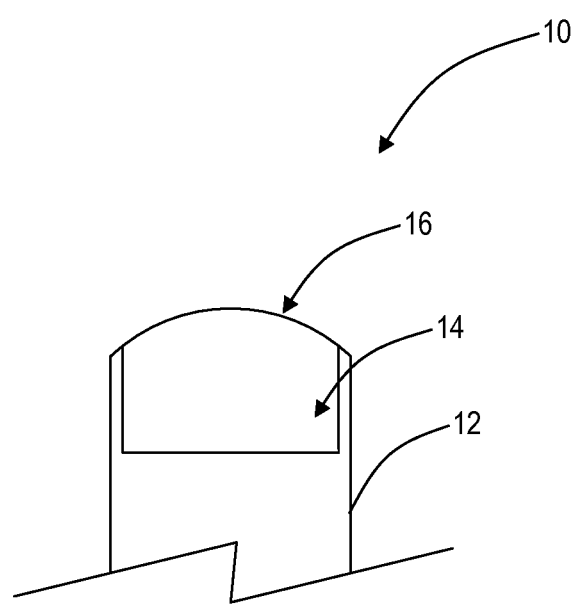
FIG. 5 illustrates one exemplary embodiment of the novel tattoo needle housing of the present invention, the tattoo needle housing including a novel tip that has a curvature or shape that substantially matches the collective curvature or shape of a plurality of enclosed tattoo needles.
Figure 6:
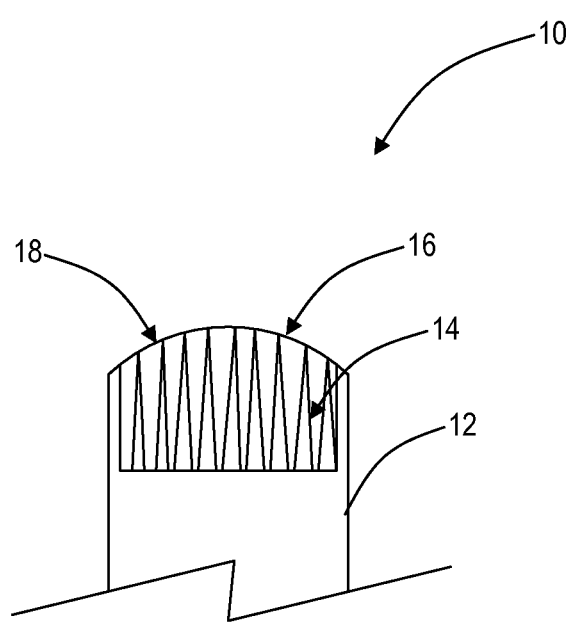
FIG. 6 illustrates one exemplary embodiment of the novel tattoo needle housing assembly of the present invention, the tattoo needle housing including a novel tip that has a curvature or shape that substantially matches the collective curvature or shape of the plurality of enclosed tattoo needles.

Referring to FIGS. 5 and 6, however, in one exemplary embodiment of the present invention, the prismatic tubular structure 12 is manufactured from titanium, another metal, a plastic material, or a ceramic material, and the bottom-front edge 16 of the prismatic tubular structure 12 has a substantially curved edge, the shape of this bottom-front edge 16 substantially corresponding to the collective curved tip configuration of the plurality of tattoo needles 18. Advantageously, this profile matching (see FIG. 6) provides more even ink distribution and prevents residual anatomical damage from the outside tattoo needles 18 when a curved tip tattoo needle configuration is used.

The tattoo needle housing 10 of the present invention is selectively coupled to a tattoo machine base that includes various mechanisms to reciprocate or vibrate the plurality of tattoo needles 18. The curved profile arrangement of the present invention may be a two-dimensional arrangement (as illustrated in FIGS. 5 and 6), or, alternatively, the curved profile arrangement of the present invention may be a three-dimensional arrangement, wherein various tattoo needles 18 are of different protrusion lengths depending on their location both horizontally and vertically, with the side profiles of the prismatic tubular structure 12 also matching the vertical profile of the curved tip tattoo needle configuration, as well as the horizontal profile of the bottom and/or top of the prismatic tubular structure 12.

Figure 7:
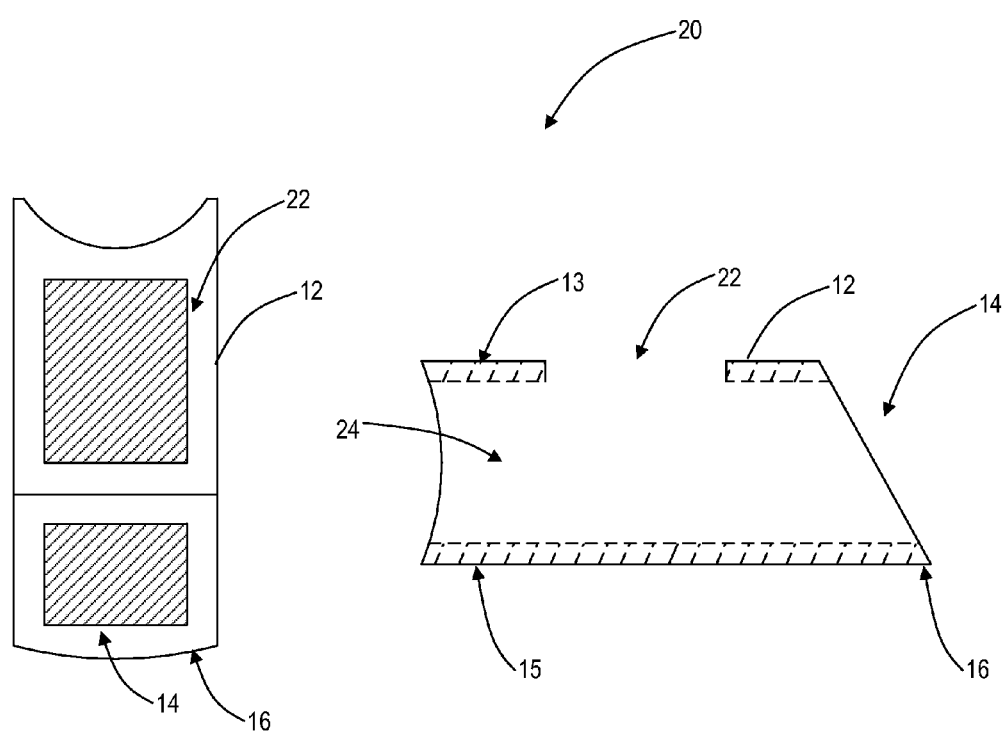
FIG. 7 illustrates another exemplary embodiment of the novel tattoo needle housing of the present invention, the tattoo needle housing including a cut away portion, or port, that, in part, forms a reservoir for more effectively retaining ink adjacent to the tattoo needles disposed in the tattoo needle housing.

Referring to FIG. 7, in another exemplary embodiment of the present invention, the tattoo needle housing 20 includes a prismatic tubular structure 12 that surrounds a plurality of tattoo needles 18 (FIG. 6) disposed therein. Again, the prismatic tubular structure 12 may have a substantially rectangular shape, a substantially square shape, a substantially oval shape, a substantially circular shape, a substantially triangular shape, an odd shape, etc. The tip of each of the plurality of tattoo needles 18 protrudes slightly through an opening 14 manufactured into the end portion of the prismatic tubular structure 12, such that the tip of each of the plurality of tattoo needles 18 may selectively contact the skin of a tattoo recipient. The top surface 13 and/or bottom surface 14 of the prismatic tubular structure 12 includes one or more openings 22, or windows or ports, manufactured therein and configured to, in part, form a reservoir or bladder 24 for more effectively retaining ink adjacent to the tattoo needles 18. Again, the bottom-front edge 16 of the prismatic tubular structure 12 may have a substantially square edge, substantially perpendicular to the axis of the prismatic tubular structure 12, substantially corresponding to the collective squared off tip configuration of the plurality of tattoo needles 18, or the bottom-front edge 16 of the prismatic tubular structure 12 may have a substantially curved edge, the shape of this bottom-front edge 16 substantially corresponding to the collective curved tip configuration of the plurality of tattoo needles 18. Preferably, the prismatic tubular structure 12 is manufactured from titanium, another metal, a plastic material, or a ceramic material.

Figure 8:
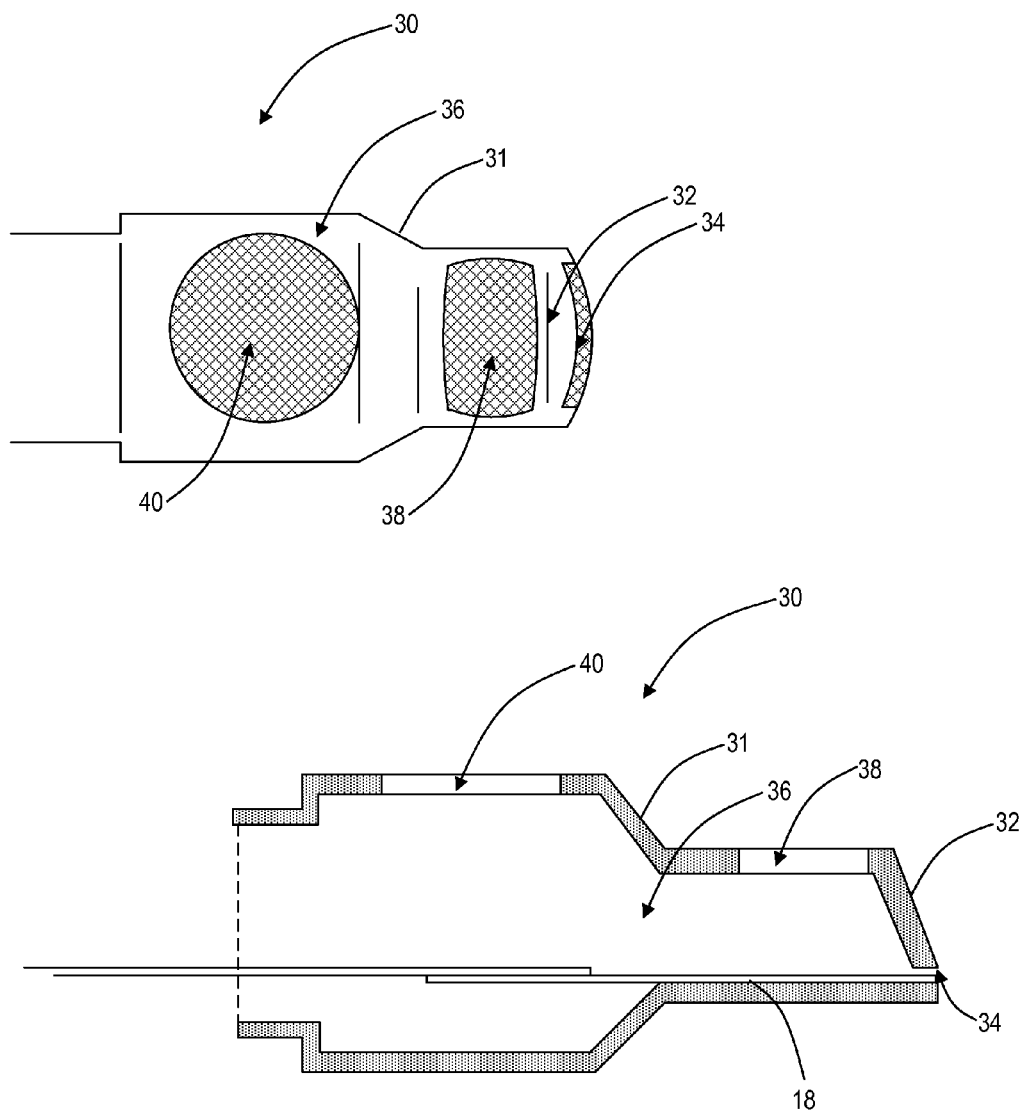
FIG. 8 illustrates a further exemplary embodiment of the novel tattoo needle housing of the present invention, the tattoo needle housing including one or more cut away portions, or ports, that, in part, form a reservoir for more effectively retaining ink adjacent to the tattoo needles disposed in the tattoo needle housing.

Referring to FIG. 8, in a further exemplary embodiment of the present invention, the tattoo needle housing 30 includes a single or multiple-piece prismatic structure 31 that surrounds a plurality of tattoo needles 18 (and, optionally, a portion of any actuating structures coupled thereto) disposed therein. Again, the prismatic structure 31 may have a substantially rectangular shape, a substantially square shape, a substantially oval shape, a substantially circular shape, a substantially triangular shape, a varying shape, an odd shape, transitional surfaces, etc. The tip of each of the plurality of tattoo needles 18 protrudes slightly through an opening 34 manufactured into the end portion of the prismatic structure 31, such that the tip of each of the plurality of tattoo needles 18 may selectively contact the skin of a tattoo recipient. In this exemplary embodiment, the end portion of the prismatic structure 31 is largely closed off by an end wall 32, such that the opening 34 is essentially a slit, and/or otherwise provides only the minimum required exposure for the plurality of tattoo needles 18. The presence of this end wall 32 assists in retaining ink in the prismatic structure 31 when it is disposed at an angle or otherwise held vertically. The top surface and/or bottom surface (or, alternatively, the side surfaces) of the prismatic structure 31 include one or more openings 38 and 40, or windows or ports, manufactured therein and configured to, in part, form a reservoir or bladder 36 for more effectively retaining ink adjacent to the tattoo needles 18. Again, the bottom-front edge of the prismatic structure 31 may have a substantially square edge, substantially perpendicular to the axis of the prismatic structure 31, substantially corresponding to the collective squared off tip configuration of the plurality of tattoo needles 18, or the bottom-front edge of the prismatic structure 31 may have a substantially curved edge, the shape of this bottom-front edge substantially corresponding to the collective curved tip configuration of the plurality of tattoo needles 18. Preferably, the prismatic structure 31 is manufactured from titanium, another metal, a plastic material, or a ceramic material, although any suitable material may be utilized.

Figure 9:
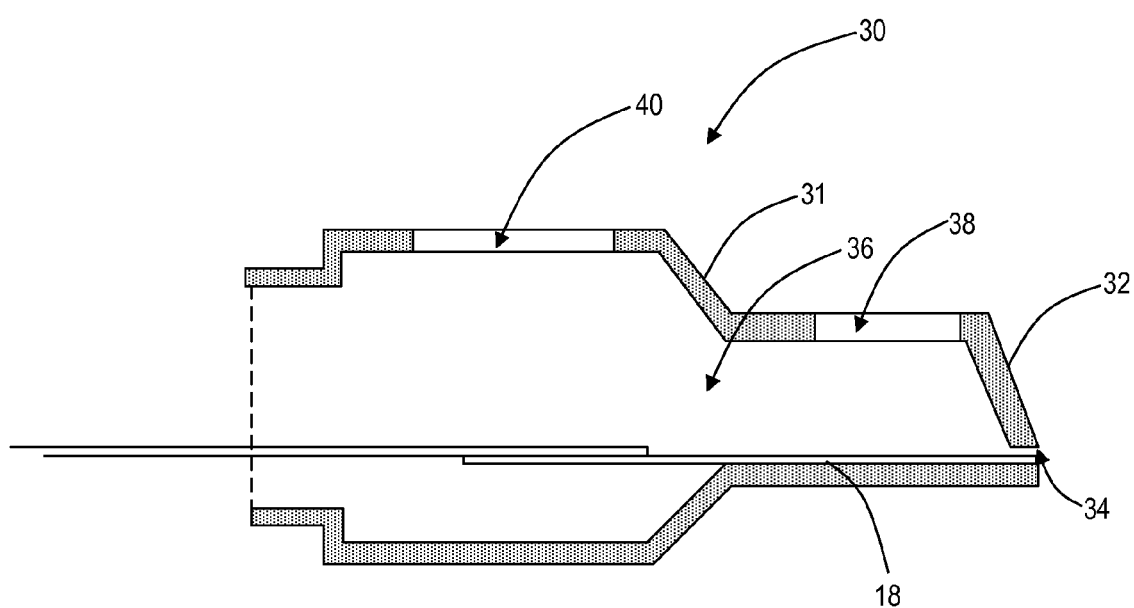
FIG. 9 illustrates a still further exemplary embodiment of the novel tattoo needle housing of the present invention, the tattoo needle housing including one or more cut away portions, or ports, and a partial end wall that, in part, form a reservoir for more effectively retaining ink adjacent to the tattoo needles disposed in the tattoo needle housing.

Referring to FIG. 9, in a still further exemplary embodiment of the present invention, the tattoo needle housing 30 includes a single or multiple-piece prismatic structure 31 that surrounds a plurality of tattoo needles 18 (and, optionally, a portion of any actuating structures coupled thereto) disposed therein. Again, the prismatic structure 31 may have a substantially rectangular shape, a substantially square shape, a substantially oval shape, a substantially circular shape, a substantially triangular shape, a varying shape, an odd shape, transitional surfaces, etc. The tip of each of the plurality of tattoo needles 18 protrudes slightly through an opening 34 manufactured into the end portion of the prismatic structure 31, such that the tip of each of the plurality of tattoo needles 18 may selectively contact the skin of a tattoo recipient. In this exemplary embodiment, the end portion of the prismatic structure 31 is largely closed off by an end wall 32, such that the opening 34 is essentially a slit, and/or otherwise provides only the minimum required exposure for the plurality of tattoo needles 18. The presence of this end wall 32 assists in retaining ink in the prismatic structure 31 when it is disposed at an angle or otherwise held vertically. The opening 34 may be disposed substantially at the bottom of the prismatic structure 31, at the top of the prismatic structure 31, or anywhere there between. The top surface and/or bottom surface (or, alternatively, the side surfaces) of the prismatic structure 31 include one or more openings 38 and 40, or windows or ports, manufactured therein and configured to, in part, form a reservoir or bladder 36 for more effectively retaining ink adjacent to the tattoo needles 18. Again, the bottom-front edge of the prismatic structure 31 may have a substantially square edge, substantially perpendicular to the axis of the prismatic structure 31, substantially corresponding to the collective squared-off tip configuration of the plurality of tattoo needles 18, or the bottom-front edge of the prismatic structure 31 may have a substantially curved edge, the shape of this bottom-front edge substantially corresponding to the collective curved tip configuration of the plurality of tattoo needles 18. Preferably, the prismatic structure 31 is manufactured from titanium, another metal, a plastic material, or a ceramic material, although any suitable material may be utilized.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A tattoo needle housing, comprising:
a substantially hollow structure configured to surround a plurality of tattoo needles, wherein the substantially hollow structure comprises a bottom edge portion at one end thereof that has a convex outward shape that substantially matches and conforms to a collective convex outward shape of the tips of the plurality of tattoo needles taken as a group, wherein the substantially hollow structure comprises one or more ports manufactured into one or more of a top surface and a bottom surface thereof, and wherein the substantially hollow structure comprises an end wall adjacent to the tips of the plurality of tattoo needles configured to form a reservoir to retain ink adjacent to the plurality of tattoo needles.

2. The tattoo needle housing of claim 1, wherein the substantially hollow structure further comprises at least one side edge portion at one end thereof that has a shape that substantially matches a collective shape of the tips of the plurality of tattoo needles.

3. The tattoo needle housing of claim 1, wherein the substantially hollow structure further comprises a top edge portion at one end thereof that has a shape that substantially matches a collective shape of the tips of the plurality of tattoo needles.

4. The tattoo needle housing of claim 1, wherein the substantially hollow structure is manufactured from a non-metallic material.

5. The tattoo needle housing of claim 1, wherein the substantially hollow structure comprises a plurality of ports manufactured into one or more of the top surface and the bottom surface thereof.

6. The tattoo needle housing of claim 1, wherein the substantially hollow structure comprises the end wall that, along with the bottom edge portion, forms a port by which access to the plurality of tattoo needles is had from the exterior of the substantially hollow structure.

* * * * *